United States Patent [19]

Bournonville

[11] Patent Number: 4,848,359

[45] Date of Patent: Jul. 18, 1989

[54] APPARATUS FOR MONITORING THE NEURO-MUSCULAR REACTION OF A PATIENT

[76] Inventor: Patrick Bournonville, Les Calhandes, 62250 Marquise, France

[21] Appl. No.: 167,973

[22] Filed: Mar. 14, 1988

[30] Foreign Application Priority Data

Mar. 13, 1987 [FR] France ............................. 87 03785

[51] Int. Cl.$^4$ .............................................. A61B 5/05
[52] U.S. Cl. .................................................. 128/741
[58] Field of Search ............... 128/741, 774, 782, 905, 128/421, 422, 420.5, DIG. 15; 340/407, 709; 273/148 B, 150, 148 R

[56] References Cited

U.S. PATENT DOCUMENTS

| | | |
|---|---|---|
| 3,794,019 | 2/1974 | Ritland et al. .......................... 128/77 |
| 4,387,723 | 6/1983 | Atlee, III et al. ..................... 128/741 |
| 4,509,383 | 4/1985 | Yeh ................................. 273/148 B |

OTHER PUBLICATIONS

"Microcomputer-Based Muscle Relaxation Monitor and Controller for Clinical Use", Bradlow et al., Medical & Biological Engineering & Computing, Nov. 1985, pp. 547–555.

Primary Examiner—Max Hindenburg
Assistant Examiner—Scott Getzow
Attorney, Agent, or Firm—Kerkam, Stowell, Kondracki, and Clarke

[57] ABSTRACT

The invention provides an apparatus for monitoring the neuro-muscular reaction of a patient more particularly, but not exclusively, for the purpose of monitoring curarization and decurarization. This apparatus is characterized in that the piston of the sensor (3) is associated with an at least substantially cylindrical body so as to slide substantially radially to the axis of the body so that, whatever the dimensions of the patient's hand, the piston (35) of the sensor can be actuated no longer by the last but by the first phalanx (10) of the thumb (4) of the hand (5) equipped with the device (1) and in that:

said body is associated with at least one stop (7) disposed so as to provide, by cooperating with at least one of the members, formed by the patient's hand and forearm, a reference for the positioning of the hand (5) along the longitudinal axis (8) of the handle, (6), and the device includes at least one means (9) for adjusting, substantially along the axis (8) of the handle (6), the relative position of the elements formed by the stop (7) and the detection means (3).

8 Claims, 3 Drawing Sheets

APPARATUS FOR MONITORING THE NEURO-MUSCULAR REACTION OF A PATIENT

The invention relates to an apparatus for checking a patient's neuro-muscular reaction particularly, but not exclusively, for the purpose of monitoring the curarization and the decurarization.

BACKGROUND OF THE INVENTION

It is now clearly established that the extent and duration of the effect of administered curare are fairly widely variable from one patient to another.

If it is then desirable to inject in the patient the amount of curare necessary for carrying out the surgical act and which is at the same time the lowest possible, it is necessary to be able to measure the degree of curarization.

Furthermore, safety of awakening depends on the most accurate evaluation possible of the decurarization (so of the residual curarization) which it is just as desirable to try and quantify whenever possible.

Quantification of curarization may be obtained by checking the secondary muscular response to stimulation of the motor nerve.;

Up to present, apparatus are known forn providing such checking (FR-A-1 359 777).

Such an apparatus comprises mainly:

an electric stimulator itself including a pulse generator connected to electrodes applied to the patient at the level of one of the passage points of the chosen motor nerve, a sensor detecting the muscular response to be monitored with means for adapting it to the patient, an analyzer analysing the signal emitted by the sensor.

The stimulator and the analyzer are obviously preferably designed so as to be able respectively to deliver different stimulations and to analyse the responses to these different simulations.

For electric stimulation, one of the cubital nerves is generally influenced and the transmission of the electric influx is ensured by members provided for this purpose such as subcutaneous electrodes or needles, which, connected to the apparatus, are disposed for example at the level of one of the wrists of said patient.

For detecting and measuring the muscular response in presently known apparatus, the sensor is disposed so as to detect and measure the adduction force at the level of the last phalanx of the thumb of the member at the level of which the stimulation is organized.

To correctly organize detection at the level of the hand concerned of the patient, it is necessary to immobilize this hand and to preposition the sensor.

For this, a device is known (US-A-4 236 528) which immobilizes one of the forearms of the patient in a position with the hand flat.

Other than a support plate against which the hand is placed, the device includes means for fixing the forearm and the hand on the plate, such as straps, and the detection member associated with the plate by a means for adjusting its position therefore allowing the device to be adapted to the dimensions of the patient's hand.

Besides it traumatic aspect for the patient and its considerable size, it is blamed for forcing the adductor of the last phalanx of the thumb to work in a plane more particularly defined by the support plate and in all cases appreciably distant from the natural adduction plane of this member which adversely affects the adduction reactions thereof.

In another device, the sensor consists of a piston sliding axially in a cylindrical body clamped in the hand which is held closed by straps and acting on a stress gauge.

Besides the problem of the wrong position involved, this apparatus also requires the piston to be acted on by the last phalanx of the thumb, therefore the reproach made to these two devices is a lack of reliability due to the numerous parasite movements of the last phalanx of the thumb and to the parasites in the environment of the patient such for example as the action of an electric surgical knife or mechanical shocks.

The signals picked up and analyzed in presently known apparatus are then, for a large part, formed of parasite signals among which it is sometimes difficult to recognize those corresponding to the expected muscular responses, which may even be drowned in the wave of parasite signals which, like the others, are in the form of peaks which are more or less pronounced, whence an extremely considerable risk of errors in the results of the analysis.

To limit the effects thereof, a device is known (medical and biological engineering and computing vol. 23 No. 6 of Nov. 1985 pps 547–555 IFMBE London, GB. H. S Bradlow et al "Microcomputer Based Muscle Relaxation Monitor and Control for Clinical Use") whose analysing circuit and stimulator are connected up so as to read the signal picked up only at the moment when it is expected.

Although, in the meantime, the wrong interpretation of simple parasites is avoided, during reading, the parasites still exist and falsify such reading.

A device is also known (US-A-4 387 723) in which a frequency band of about 10 Hz of the signals received is systematically eliminated, which eliminates the corresponding parasites but does not take into account the developmenet of noise and either parasites continue to exist or the signals picked up are amputated for no reason.

Moreover, if it were only for a greater linearity of the response detected, instead of being simply applied against the member where the response is expected, the piston of the sensor is generally applied against said member with a certain force called "preload" which depends on different factors such as the sensitivity of the patient to pulses.;

Unfortunately, these factors may themselves evolve during the time that the analysis lasts and falsify the result.

BRIEF SUMMARY OF THE INVENTION

A result which the invention aims at obtaining is an apparatus which is less traumatizing and which lets the member work in its normal plane of adduction.

A further result of the invention is that such an apparatus is less subject to parasite movements of the member.

Another result which the invention obtains is an apparatus of the above type protected from the influence of the noises of the environment.

A further result which the invention aims at obtaining is such an apparatus allowing adaptation as a function of the foreseeable modification of the required preload.

For this, the invention provides an apparatus of the above type, including at least one device for maintaining the sensor in an adequate position for detecting the adduction movement of the thumb of one of the hands, which device includes a piston sliding with the respect to a body at least substantially cylindrical and clenched in the hand of the patient in the manner of a handle, this apparatus being characterized in that the piston of the sensor is associated with the at least substantially cylindrical body so as to slide substantially radially to the axis of the body so that, whatever the dimensions of the patient's hand, the piston of the sensor can be actuated no longer by the last but by the first phalanx of the thumb of the hand equipped with the device and in that:

said body is associated with at least one stop disposed so as to provide, by cooperating with at least one of the members, namely the patient's hand and forearm, a reference for the positioning of the hand along the longitudinal axis of the handle, the device includes at least one means for adjusting, substantially along the axis of the handle, the relative position of the elements formed by the stop and the detection means.

BRIEF DESCRIPTION OF THE INVENTION

The invention will be better understood from the following description given by way of non limitative example with reference to the accompanying drawings which show:

DETAILED DESCRIPTION OF THE INVENTION

Figure 1:
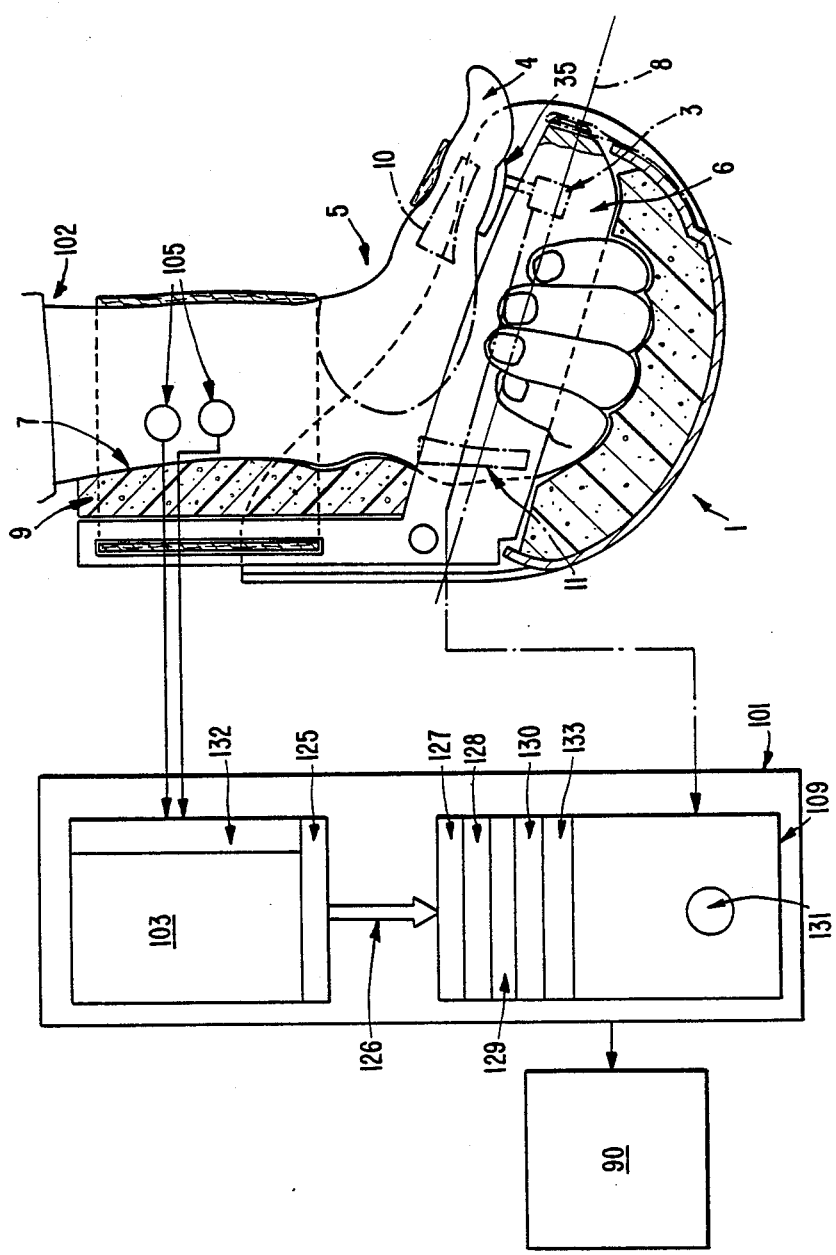
FIG. 1: the block diagram of the apparatus.
Figure 2:
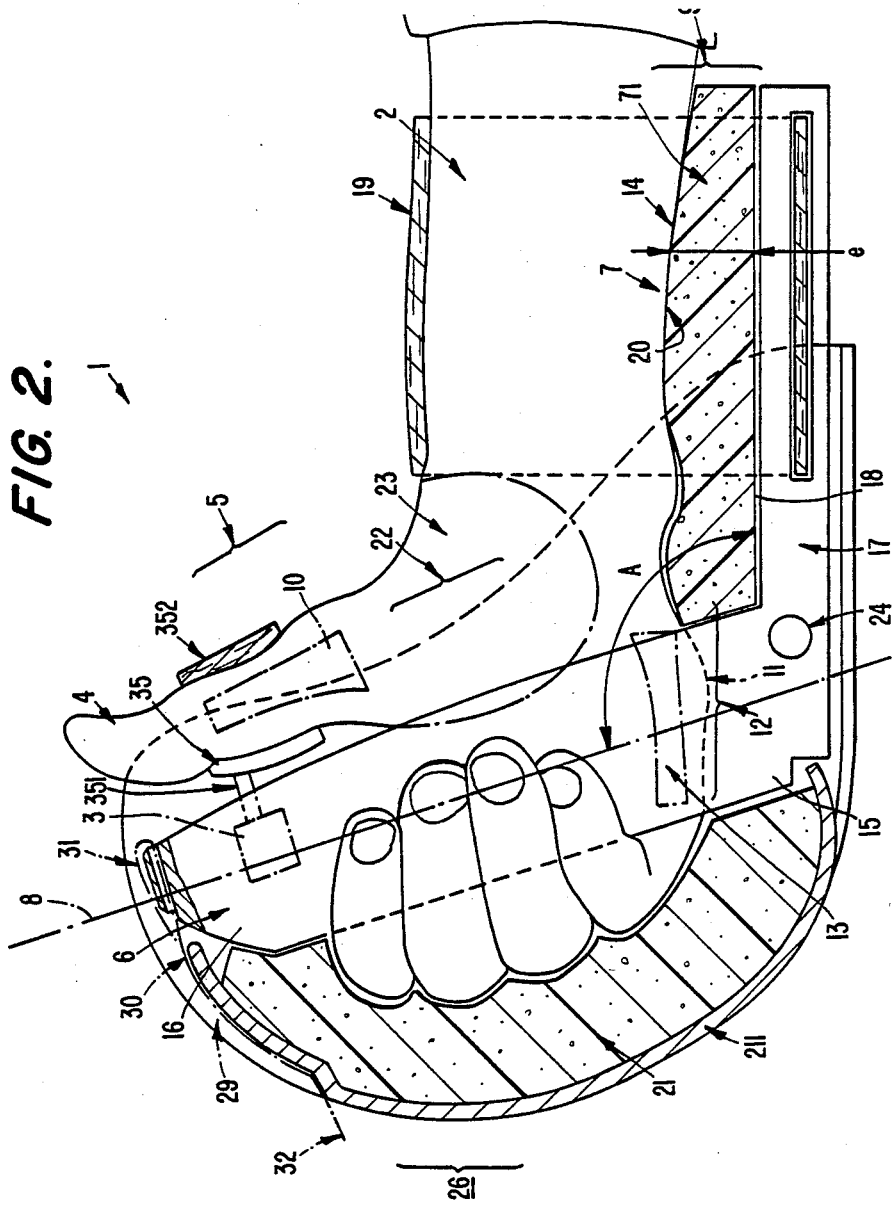
FIG. 2: the device seen in section showing the position of the hand and of the fingers on the handle.
Figure 3:
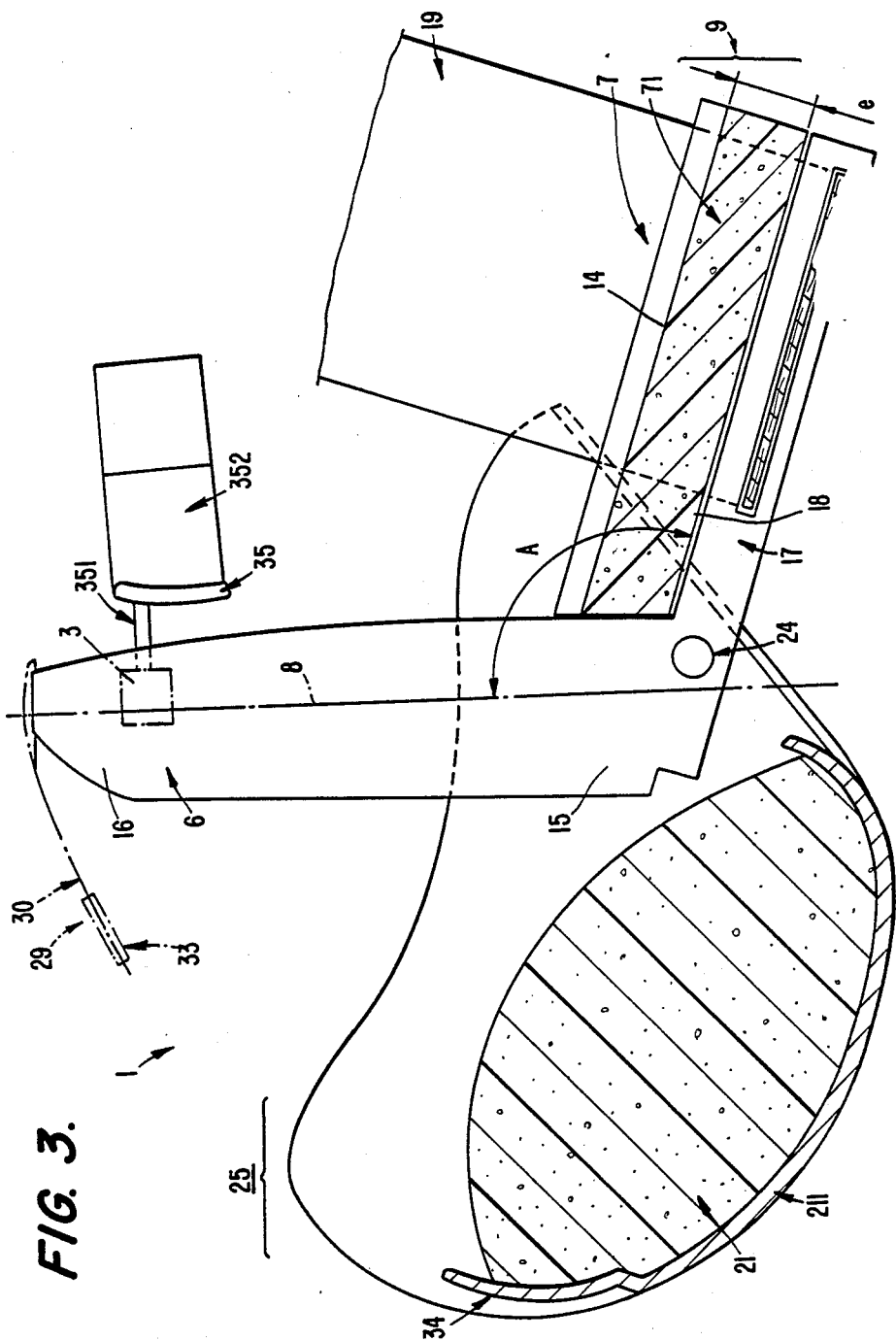
FIG. 3: the device seen through the same sectional plane in a released position.

Referring to the drawings, an apparatus 101 is shown for monitoring the neuro-muscular reaction of a patient 102, which apparatus can for example be used for monitoring curarization and/or decurarization by means of:

a stimulator 103 itself including a pulsed generator and, connected to the generator, electrodes 105 applied to the patient 102 at the level of one of the passage points of the chosen motor nerve such as the cubital nerve, a sensor 3 detecting the muscular response to be monitored, including a stress gauge with means for adapting to the member 4 on which the response is to be picked up, an analyzer 109 analysing the signal emitted by the sensor 3, which stimulator 103 and analyzer 109 comprise means for emitting different stimulations and for analysing the responses to these different stimulations.

In any case, the apparatus comprises at least one device 1 for maintaining the sensor 3 in an adequate position for detecting the adduction movement of the thumb 4 of one of the hands 5, which sensor comprises a piston 35 sliding with respect to a body 6 which is at least substantially cylindrical and is gripped by the patient's hand in the manner of a handle.

According to an essential characteristic of the invention, this apparatus is characterized in that the piston 35 of sensor 3 is associated with the at least substantially cylindrical body 6 so as to slide substantially radially to the axis 8 of body 6 so that, whatever the dimensions of the patient's hand, the piston 35 of the sensor can be actuated no longer by the last but by the first phalanx 10 of the thumb 4 of the hand 5 equipped with the device 1 and in that:

said body 6 is associated with at least one stop 7 disposed so as to provide, by cooperating with at least one of the members formed by the patient's hand and forearm, a reference for the position of the hand 5 along the longitudinal axis 8 of the handle 6, and the device includes at least one means 9 for adjusting, substantially along the axis 8 of handle 6, the relative position of the elements formed by the stop 7 and the sensor 3.

According to the invention, stop 7 cooperates at least locally with the edge 11 of the hand equipped with the device particularly in the zone 12 of the metacarpal of the little finger 13 so as to establish the position of this hand as defined above.

In a preferred embodiment, stop 7 is formed by an elongate flange 71 whose surface 14 bearing against the patient's member extends beyond handle 6 and cooperates not only with the edge 11 of the hand but also with a fraction of the forearm situated in the extension thereof.

In another embodiment, it is the elongate flange 71 which forms the means for adjusting the relative position of piston 35 and of stop 7 substantially in the longitudinal axis 8 of the handle and, for this, it is chosen with a thickness "e" at least sufficient so that, cooperating by its face 14 with the side of the patient's forearm, the sensor 3 can be actuated by the first phalanx of the patient's thumb.

Advantageously, the longitudinal axis of handle 6 forms with stop 7 an angle A substantially greater than 90° and, preferably, substantially equal to 105°.

To associate stop 7 with the end 15 of handle 6 opposite that 16 near which sensor 3 is situated, said handle 6 is fixed to a plate 16 which extends substantially parallel to the axis of the forearm.

This plate 16, which receives stop 7 by its face 18 opposite the bearing face 14, has means 19 for fixing to the fraction of the forearm situated facing stop 7.

In accordance with the invention, for adapting the fingers of the hand about the handle, the device comprises a cushion 21 of a shape for, on the one hand, amply enveloping the patient's hand while restraining it resiliently at least at the level of the fingers gripping the handle but also to constantly free the zone 22 of the adduction muscle 23 of the thumb, which cushion is combined with a support element 211 connected to the handle by a connection means 24 providing movement of cushion 21 at least between two end positions 25, 26 one position 25 in which the cushion totally frees the acess to the handle so that it can be gripped by the patient and another position 26 in which it amply envelopes the patient's hand as defined above for holding his fingers resiliently closed on the handle.

Preferably, rather than translational guiding which nevertheless remains possible, the connection means 24 consists of an articulation 24 whose axis is substantially orthogonal to the plane passing through the longitudinal axis 8 of handle 6.

Advantageously, cushion 21 is made from a flexible cellular synthetic material.

The support element 211 for cushion 21 consists of a rigid shield which surrounds said cushion 21 externally so as to be able to induce an optimal resilient contact between this latter and the patient's fingers closed on handle 6.

The two end positions 25, 26 of shield 211 are defined by stop members positioned appropriately on the two mobile elements formed by shield 211 and the assembly comprising handle 6 and the elongate plate 17 which is associated therewith.

To hold shield 211 in position 26 enveloping the patient's hand equipped with the device, this latter comprises of course a locking means 29 which is formed for example of a tie 30 one end of which 31 is anchored at the top of handle 6 and the free end 32 of which is equipped with an element 33 for removable connection with a given point 34 of the shield.

For forming the removable connection element 33 and its anchorage point 34, pieces of self gripping fabrics are used well known under the name VELCRO.

Piston 35 for actuating the stress gauge includes a means 352 for connecting the thumb to the piston.

Advantageously, this connection means is formed of a strap for clamping the patient's thumb and applying a preferably adjustable preload to the piston.

Advantageously, the device itself carries directly the stimulation electrodes 105 even the other elements of the device formed by all or part of the stimulator and/or of the analyzer taken separately or with at least some of their accessories such as means for displaying the signals picked up and/or a display showing the results of the analysis.

The analyzer may be connected to an automatic curare injection apparatus.

Besides the means for displaying the signal picked up and/or a display showing the results of the analysis, this analyzer may be connected to an assembly 90 of peripheral apparatus and more particularly:

an interface for communication with, for example, a keyboard, a plotting table, a circuit for connection to an electric surgical knife.

Stimulator 103 may comprise, when this type of power supply is chosen, a means for measuring the charge level of the supply battery (not shown), even an alarm placed under its control.

The apparatus is further provided with:

with complementary means 125, 126 and 127 for informing the analyzer 109 by the stimulator 103 of the times when each of the stimulations is emitted, with a means 128 which, taking into account this information and the delay between the emission of a stimulation and recepton of the corresponding reaction signal, distinguishes in the signal picked up, with a certain tolerance, the periods when the possible reaction signals occur from the other periods during which only parasite signals are picked up.

In accordance with the invention, the apparatus further comprises:

a means 129 which, during the periods when only parasite signals may be picked up, measures the level of the detected signal, and a means 130 which eliminates from the detected signal only the band corresponding to the measured noise signals, which means is preferably situated between sensor 3 and means 128 for distinguishing the period so as to form a continuous regulation loop.

Such synchronization of the stimulation and analyzer and such filtration means that the signal fed to the means analysing the responses to the stimulations is free of surrounding noise whatever its evolution.

The signal and the result from the apparatus are therefore more reliable.

The stimulator comprises a means 131 for progressively adjusting the strength of a signal so as to obtain the desired level.

Advantageously, the stimulator 103 includes a means for maintaining the emitted signal not at a constant voltage but at a constant current and thus the responses remain insensitive to the impedance variations between the electrodes 105 and the conducting paste or the patient himself.

The analyzer also includes a calibration means 133 for calibrating the detected signal for adapting a reference signal proper to each case to the width of the reading scale.

According to a characteristic of the invention, it will be a question of a variable gain amplifier with automatic adjustment.

It is obvious that numerous modifications may be made to the apparatus without for all that departing from the scope and spirit of the invention.

I claim:

1. An apparatus (101) for checking a patient's (102) neuro-muscular reaction which may for example be used, for monitoring curarization and/or decurarization comprising:

stimulator means (103) including a pulse generator and electrodes (105) connected to the generator and appliable to a patient (102) at a chosen motor nerve such as the cubital nerve of the forearm of a patient, sensor means (3) for detecting the muscular response to be monitored and comprising a stress gauge and means for adapting the sensor to a patient thumb (4), analyzer means (109) for analysing a reaction signal emitted by the sensor (3), which stimulator 103 and analyzer 109 comprise means for emitting different stimulations and analyzing the responses to these different stimulations, and, complementary means (125, 126 and 127) for informing the analyzer (109) by the stimulator (103) of the times when each of the stimulations are emitted, and means (128) which taking into account this information from said complementary means and the delay between the emission of a stimulation and reception of the corresponding reaction signal, distinguishes in the signal picked up, the periods when the possible reaction signals occur from the other periods during which only parasite signals are picked up, and further comprising a holding device consisting of a handle (1) for maintaining in one end said sensor means (3) in a position for detecting the adduction movement of a patients thumb (4) said sensor includes a piston sliding with respect to a body and adapted to be clenched in the hand of the patient in the manner of a handle, being characterized in that the said piston (35) of said sensor means (3) is associated with said handle so as to slide substantially radially to the axis of said handle so that, whatever the dimensions of the patient's hand, said piston (35) of said sensor means can be actuated by the first phalanx (10) of the thumb (4) of the hand (5) gripping said handle and in that:

said handle is associated with at least one stop (7) disposed so as to provide, by cooperating with the patient's hand and forearm, a reference for the positioning of the hand (5) along the longitudinal axis (8) of the handle, (6) and the device includes at least one means (9) for adjusting, substantially along the axis (8) of said handle (6), the relative position of the elements formed by said stop (7) and said sensor means (3).

2. The apparatus as claimed in claim 1, characterized in that the angle formed by the longitudinal axis of said handle with said stop (7) is an angle (A) substantially greater than 90°.

3. The apparatus as claimed in claim 2, characterized in that said angle (A) is substantially equal to 105°.

4. The apparatus as claimed in claim 1, characterized in that, in order to associate said stop (7) with the end (15) of the handle opposite the end near which the sensor is situated, said handle (6) is fixed to a plate (17) which in use, extends substantially parallel to the axis of the forearm and said plate, which receives said stop (7) and has means (19) for securing a patients forearm on said stop (7).

5. The apparatus as claimed in claim 1, characterized in that, for adapting said fingers of the hand about the handle, the device comprises a cushion (21) of a shape for, amply enveloping the patient's hand while restraining it resiliently, which said cushion is combined with a support element (211) connected to said handle by a connection means (24) providing movement of said cushion (21) at least between two operative positions (25, 26) one position (25) in which the cushion totally frees the access to said handle so that it can be gripped by the patient and another position (26) in which it amply envelopes the patient's hand as defined above for holding his fingers resiliently closed on said handle.

6. The apparatus as claimed in claim 5, characterized in that said support element (211) consists of a rigid shield which surrounds said cushion (21) externally so as to be able to provide an optimal resilient support when the patient's fingers are closed on handle (6).

7. The apparatus as claimed in claim 1 including a means (352) for connecting the patients thumb to the piston, characterized in that said connection means (352) consists of a strap for clamping the patient's thumb and applying to the piston a preload which is preferably adjustable.

8. The apparatus as claimed in claim 1, characterized in that it comprises, in combination:
  means (129) which, during the periods when only parasite signals may be picked up, measures the level of the detected signal, and
  means (130) for eliminating from the detected signal only the band corresponding to the measured noise signals, said eliminating means (130) being situated between sensor (3) and means (128) for distinguishing the periods so as to form a continuous regulation loop.

* * * * *